United States Patent [19]
Lassal et al.

[11] Patent Number: 6,132,418
[45] Date of Patent: Oct. 17, 2000

[54] MULTIFUNCTION CONNECTION DEVICE, THERAPEUTIC TREATMENT DEVICE AND ITS UTILIZATION

[75] Inventors: Olivier Lassal, Saint Priest; Alexira Garin, Lyons; Francois LaCoste, Rueil Malmaison, all of France

[73] Assignee: Technomed Medical Systems, Vaulx-en-Velin, France

[21] Appl. No.: 09/233,802

[22] Filed: Jan. 19, 1999

[51] Int. Cl.[7] .................................................. A61M 25/16
[52] U.S. Cl. ...................... 604/535; 604/533; 604/534; 604/537
[58] Field of Search ................................... 604/905, 533, 604/534, 535, 537

*Primary Examiner*—Wynn Wood Coggins
*Assistant Examiner*—Manuel Mendez
*Attorney, Agent, or Firm*—Welsh & Katz, Ltd.

[57] ABSTRACT

This invention is a connection device that includes a housing whose shape is suited to be connected to a reception device. The connection device has several orifices including at least one electrical connection element and at least two sealed connection elements for a liquid. At least two of the connection elements are arranged coaxially in the same orifice. The orifices receiving the elements are arranged to cooperate in an aligned manner with connection reception elements of the reception device.

23 Claims, 6 Drawing Sheets

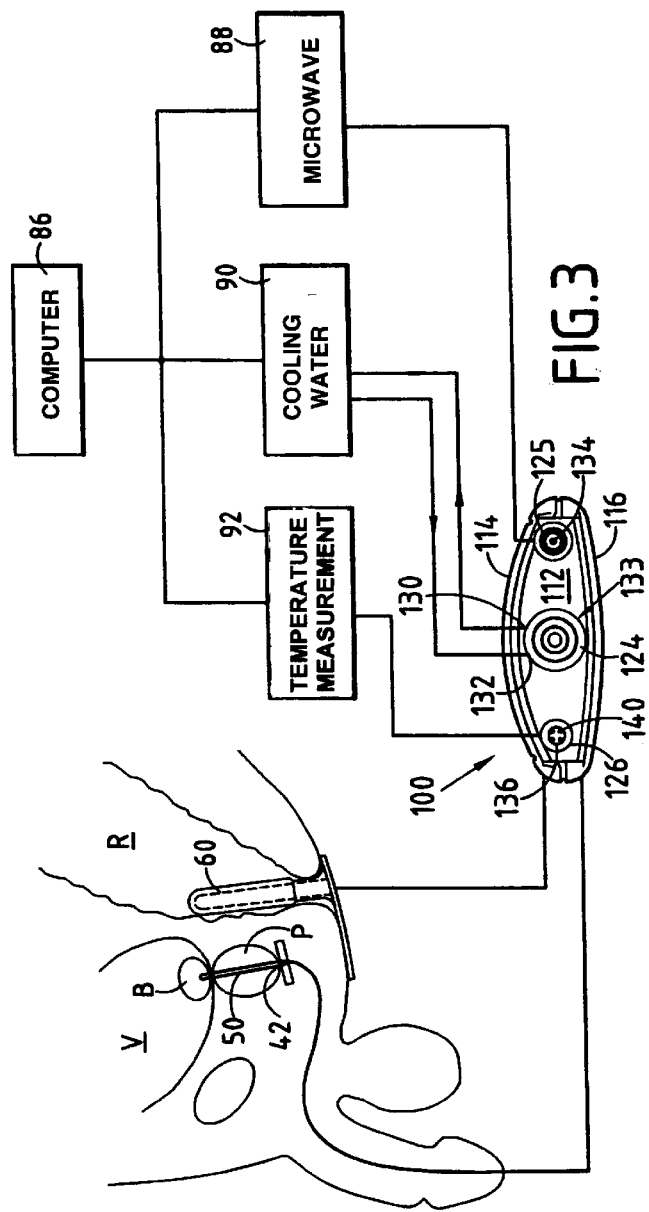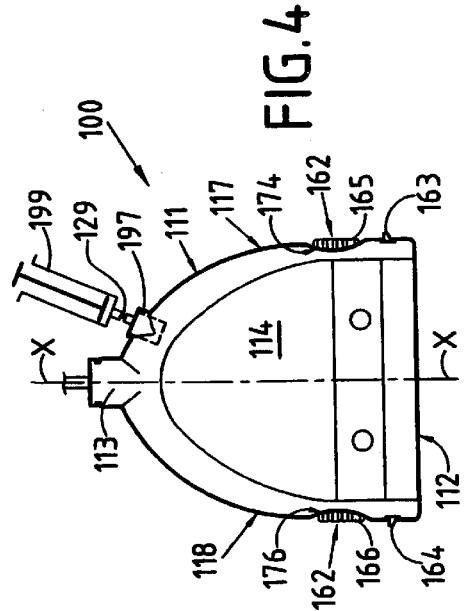

MULTIFUNCTION CONNECTION DEVICE, THERAPEUTIC TREATMENT DEVICE AND ITS UTILIZATION

BACKGROUND

The invention concerns essentially a single-piece multifunction and hybrid connection device, a therapeutic treatment device it is part of, as well as its use for the manufacture of a therapeutic treatment device.

In the framework of therapeutic treatment devices, especially those used for treatment with electromagnetic radiation and in particular microwaves, it has become necessary for the past several years to simultaneously protect certain tissues, for example the rectal wall or the urethral wall, by circulating a temperature controlled liquid, in particular water or an aqueous solution. This has been done by introducing a catheter into natural routes such as the rectum or the urethra which comprises an emitter of electromagnetic radiation, preferentially microwaves, as well as a circuit for introducing and draining the temperature controlled liquid.

The applicant, in the case of a device marketed under the name PROSTATRON®, has introduced a device for multifunction and hybrid connection, enabling seven different functions to be connected in a single operation. This connection device is depicted in FIGS. 1 and 2 in appendix. This is a single-piece device including a housing with a shape suitable to connect into a reception device, including a front face, a rear face, an upper face and a lower face, and lateral linking faces, said front face including several orifices in which the various elements to connect are inserted, including at least one electrical connection element and at least two elements for the water tight connection of a liquid, for example water or an aqueous solution, the said orifices receiving the said elements being spaced over the said front face, in positions aligned with connection reception elements of the connection reception device.

Nevertheless, this previous multifunction and hybrid connection device of the applicant marketed in the context of its PROSTATRON® device includes on its front face six orifices of which two are used exclusively to align centering pins on the reception device arranged as far apart as possible for better centering. In addition, the connection elements for liquid inlets and outlets are arranged in two orifices having practically the same distance between them as the centering orifices. The latter two orifices are located more centrally and are used for the passage of an element for the transmission of the electromagnetic radiation, preferentially microwaves, and a temperature detection element, preferentially optical fibers that arrive flush on the surface of the front face of the connection device, such that no direct centering of the optical fibers is possible, as this only results from the alignment of the centering pins connecting into the centering orifices in the front face of the connection device. The use of optical fibers is preferred for measuring temperature when the electromagnetic radiation is microwaves, since optical fibers enable temperature to be measured without being disturbed by the microwave environment. This previous connection device also includes an orifice in the lower face for the passage of a conduit for inflating a balloon located in front of the therapeutic treatment probe.

Thus, this device preceding the invention is complex and costly and does not insure the direct alignment of the optical fibers. To obtain a precise alignment of the optical fibers, it is thus necessary to precisely machine the parts to obtain a practically perfect centering using the centering pins and the centering orifices. This precludes the use of plastic, and demands the manufacturing of a costly metal part. There is interest in using a plastic part since product disposal is simplified.

In the course of intense research by the applicant, the applicant posed the new technical problem involving the supply of a solution that will reduce the number of connection points.

Furthermore, the applicant has also posed as new technical problem the supply of a solution that will enable the self-alignment of each connection element opposite the reception device of the apparatus, in particular temperature detection elements and above all in the case where optical fibers are used.

Another aim of the present invention is to resolve the new technical problem involving the supply of a solution that enables the presence of centering pins to be avoided that create unsatisfactory ergonomics and a hyperstatic situation, at the same time assuring a perfect alignment of the multifunction and hybrid connection elements. These include at least the elements of liquid circulation and electrical connections, that by principle may generate a risk of short-circuits.

An additional aim of the invention is to resolve the new and above-mentioned technical problem even in the case where at least one connection element involves optical fibers that require perfect alignment for the correct transmission of light for a correct detection of temperature, since the diameter of these optical fibers is usually about 0.2 mm or 200 $\mu$m, and alignment must thus be precise in proportion to this diameter, meaning a precise alignment of the order of 20 $\mu$m.

SUMMARY OF THE INVENTION

For the first time, the present invention resolves all these technical problems simultaneously, reliably, usable at the industrial and medical scales, at a much lower cost than previous solutions and in particular compared to the previous solution of the PROSTATRON® device, by enabling the unexpected utilization of a totally plastic connection device, which is more suited to the single use of therapeutic treatment probes, which is evidently a determinant advantage of the invention.

Thus and according to an initial aspect, the invention concerns a single-piece multifunction and hybrid connection device that includes a housing whose shape is suited to be connectable with a reception device, comprising a front face, a rear face, an upper face, a lower face and lateral linking faces, the said front face having several orifices in which various connection elements are inserted, including at least one electrical connection element and at least two sealed liquid connection elements for a liquid, for example water or an aqueous solution, the said orifices receiving the said elements being arranged on the said front face, in positions suitable for an aligned cooperation with the connection reception elements of the connection reception device, characterized in that, with a view towards reducing the number of connection points, and improving connection ergonomics, at least two of the connection elements are arranged coaxially in the same orifice and cooperating with at least two reception connection elements also arranged coaxially.

According to an advantageous realization of the invention, the said at least two connection elements arranged in the same orifice, respectively constitute one element for the supply of a liquid and one element to drain a liquid arranged coaxially in a single part introduced in a single orifice of the said front face.

According to yet another mode of advantageous realization of the invention, the device comprises at least four connection elements installed in at least three mutually separated orifices and aligned on the said front face of the connection device, at least two of the connection elements being placed coaxially in one of the said three aligned orifices.

According to yet another mode of advantageous realization of the invention, the two coaxial connection elements are installed in a single orifice arranged practically along the longitudinal axis of the said connection device, such that the said at least two other aligned orifices are arranged preferentially on either side of the said axial orifice receiving the said two coaxial connection elements.

According to yet another mode of advantageous realization of the invention, the device includes on at least two opposing faces of the said device, other than the front and rear faces, provisional means for temporarily attaching the said connection device with the corresponding reception device.

According to yet another mode of advantageous realization of the invention, the provisional locking means include at least one means of locking and a second means of locking on the two opposing faces of the said connection device, other than the front and rear faces, the said locking means being switchable between a locked and unlocked position, and planned to enable the unlocking of a locked position of the connection device with the reception device.

According to yet another mode of advantageous realization of the invention, the above-mentioned first and second means of locking include a part that is accessible from the exterior to ensure unlocking without the use of a tool.

According to yet another mode of advantageous realization of the invention, the above-mentioned means of temporary locking are attached to the front face of the said device.

According to yet another mode of advantageous realization of the invention, the above-mentioned front face and the above-mentioned means of locking are single-piece construction, preferably in plastic, the said means of locking being preferentially defined by an extension to the interior of the connection device, i.e. on the connection part of the front face opposite the reception device, the said extension including a bend so that the extremity of the extension is near the front face, thus presenting an elongated U-shaped form, of which one branch of the U is attached to the inner side of the front face and the other extremity is mobile and has at least one anchor point to constitute a locked or unlocked position depending on whether this mobile extremity is or is not connected to the said anchor point.

According to yet another mode of advantageous realization of the invention, the branch of the mobile U includes a reinforced zone that serves as an unlocking button for releasing the connection device when it is connected to the reception device.

According to yet another mode of advantageous realization of the invention, the free extremity of the branch of the mobile U includes a part that protrudes radially towards the exterior, defining a ratchet for the easy introduction of the connection device into the reception device but which automatic locks after introduction such that an unlocking operation is necessary to release, for example by acting on the above-mentioned unlocking button.

According to yet another mode of advantageous realization of the invention, the above-mentioned front face includes at least on its lateral edges at least one notch for receiving and guiding the mobile extremity of the branch of the U, thereby constituting the above-mentioned anchor point.

According to yet another mode of advantageous realization of the invention, at least one above-mentioned connection element is a connection element of a heat detection element, preferentially optical fibers, preferentially including several optical fibers in a single connection element that is preferentially self-centering.

According to yet another mode of advantageous realization of the invention, the optical fiber connection element presents at least one flat or flattened face that provides its orientation, cooperating with a corresponding flat or flattened face of the orifice of the said front face of the connection device.

According to yet another mode of advantageous realization of the invention, the above-mentioned electrical connection element transmits electromagnetic radiation, preferentially microwaves, in particular to carry out a therapeutic treatment of an adenoma or a prostate cancer via the rectal or urethral route.

According to yet another mode of advantageous realization of the invention, the electrical connection element is an electrical connection element for the transmission of electromagnetic radiation, preferentially microwaves, in particular to carry out a therapeutic treatment of an adenoma or a prostate cancer, via the rectal or urethral route, and the liquid connection element is a coaxial two-way liquid connector for supplying and draining liquid, without locking, including sealing gaskets and a means of tightening play, a third connection element being planned on to connect a temperature detection element, preferentially optical fibers, all these elements cooperating to ensure preferentially an therapeutic treatment, in particular to carry therapeutic treatment of an adenoma or a prostate cancer, with control by the said liquid of the heating temperature of the said electromagnetic radiation, preferentially microwaves.

According to yet another mode of advantageous realization of the invention, the device includes only three connection points aligned on the said front face of the connection device, including one electrical connection point, one coaxial connection point for the two water channels, and one temperature measurement connection point, preferentially optically.

According to yet another mode of advantageous realization of the invention, at least some of the connection elements are equipped with devices for tightening play. Again preferentially, the connection device according to the invention presents only one fixed connection point defined by a connection element with precise connection, the other connection elements being relatively imprecise connection elements, equipped with devices for tightening play. These devices for tightening play may, for example, include a device with sealing gaskets, such as O-rings for example for the connection(s) of water elements, or a blade device or similar, well known by someone familiar with the technology, for example for the connection of electromagnetic radiation transmission elements, preferentially microwaves. In this preferred mode of realization including only one fixed connection point, ergonomics of the connection are fundamentally simplified, preventing or limiting a hyperstatic situation.

According to yet another mode of advantageous realization of the invention, the device is composed of two complementary and mutually lockable elements and defining the upper, lower, lateral and rear faces of the connection device, resulting in the said device being single-piece, the said front face being preferentially defined by a separate part that includes the above-mentioned provisional means of locking.

According to yet another mode of advantageous realization of the invention, the two complementary and mutually lockable elements and defining the above-mentioned connection device are asymnmetrical, i.e. the plane of junction is not a plane of symmetry of the device, in order to assure a prepositioning of the connection device with the reception device by ensuring fault-free connection to prevent a reverse connection, i.e. 180°. Advantageously, the outer surface of each of the two complementary and mutually lockable elements is used for a pre-guiding for better presentation of the above-mentioned connection elements with reference to the reception device. In the framework of the invention, it is possible and preferable to construct the connection device, and optionally the reception device, in a synthetic material, in particular plastic, without degrading the precision of the connection, even in the case where one connection element at least is used for the connection of optical fibers, which is a particularly unexpected advantage of the invention.

According to yet another mode of advantageous realization of the invention, the two above-mentioned complementary elements include at least one flared part defining by complementarity at least one output orifice on the rear part of a therapeutic treatment probe comprising at least one electromagnetic radiation emitter, preferentially microwaves, at least one element for supplying liquid and at least one element for draining liquid coaxially arranged and at least one temperature detecting element, preferentially composed of optical fibers.

According to yet another mode of advantageous realization of the invention, the two above-mentioned complementary elements including at least one second flared part that in mutual cooperation define a second output orifice towards the rear face of the device, for the reception of a conduit for inflating a balloon probe fitted on the proximal extremity of the above-mentioned therapeutic treatment probe including or on which a tap or valve system can be attached.

According to a second aspect, the present invention also covers the use of the above-mentioned connection device for the construction of a therapeutic treatment device, preferentially for the treatment of an adenoma or a prostate cancer.

According to a third aspect, the invention also covers a therapeutic treatment device characterized in that it comprises a multifunction device connection as previously defined, this apparatus being preferentially adapted to carry out a therapeutic treatment of an adenoma or prostate cancer, in particular by an electromagnetic radiation preferentially microwaves, via the rectal or urethral route.

The invention simultaneously resolves the technical problems enumerated above and the above-mentioned determinant technical advantages are obtained very simply, inexpensively, and are usable at the industrial and medical scales.

BRIEF DESCRIPTION OF THE DRAWINGS

FIG. 3 is a schematic view of a multifunction connection device according to the present invention.

FIG. 4 is a side view of the multifunction connection device of the present invention.

DETAILED DESCRIPTION OF THE PREFERRED EMBODIMENT

Figure 1:
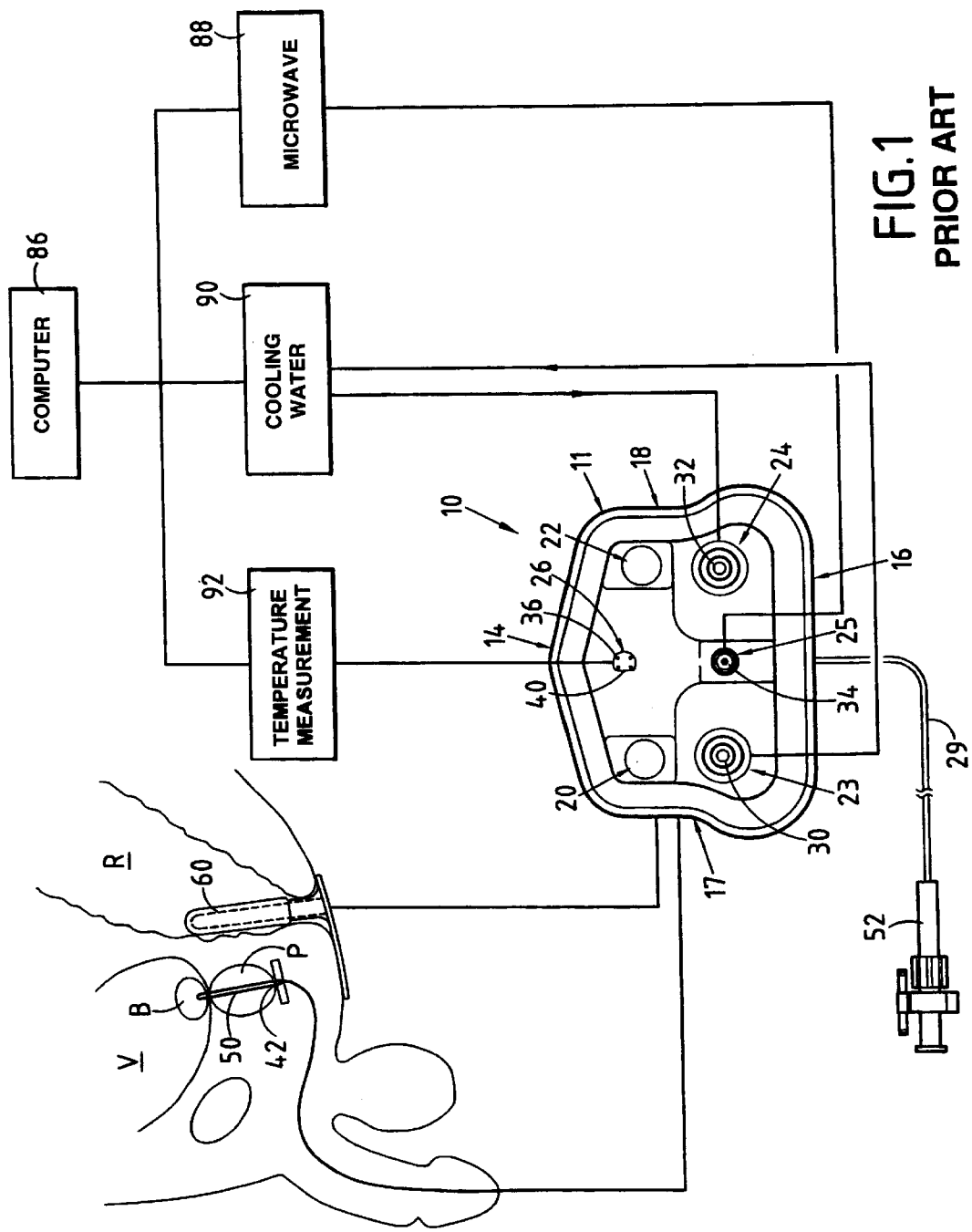
FIG. 1 is a schematic view of a prior art connection device.
Figure 2:
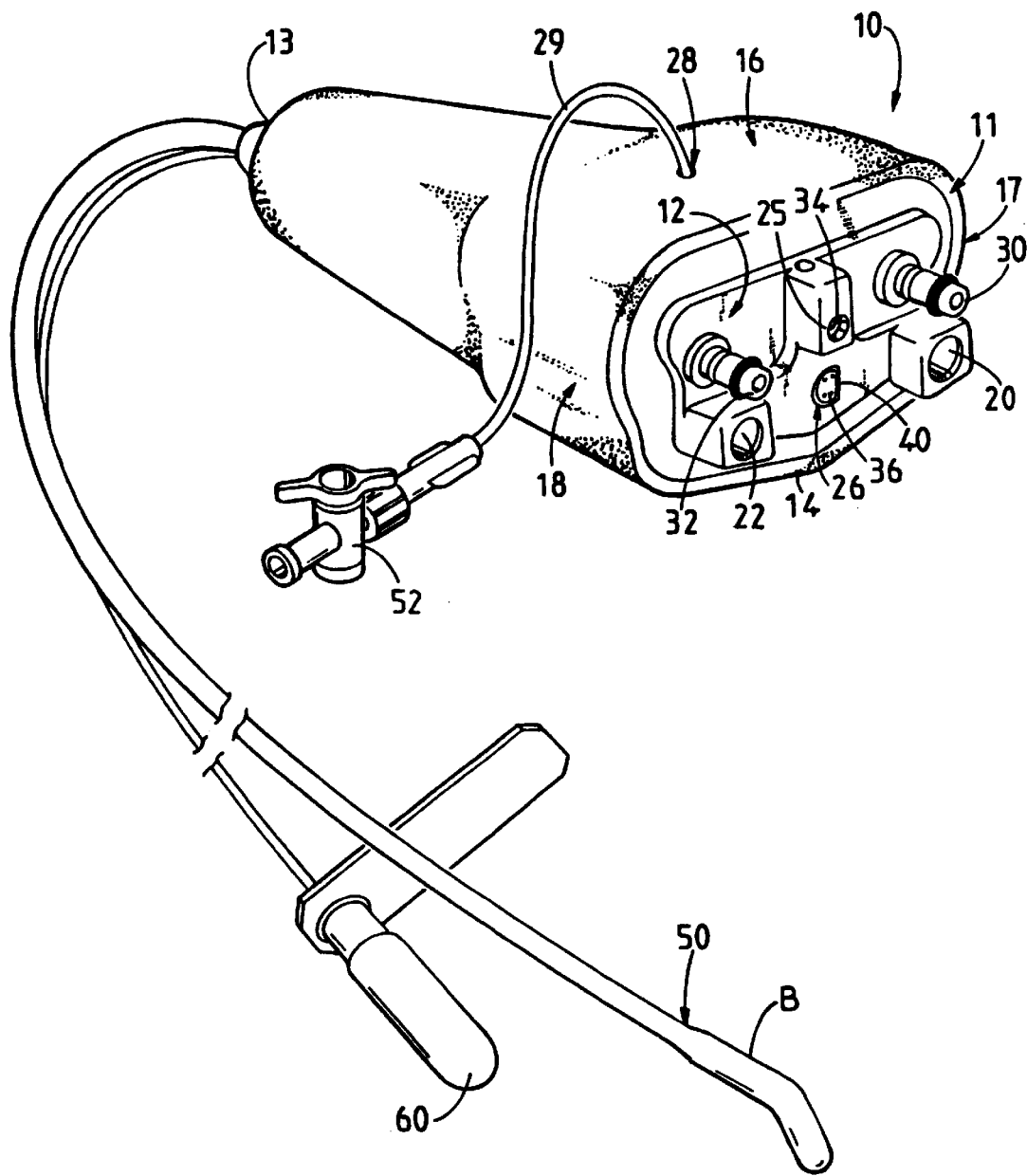
FIG. 2 is a perspective view of the prior art connection device illustrated in FIG. 1.

Other aims, characteristics and advantages of the invention will appear clearly after the explanatory description that will follow, with reference to appended drawings in FIGS. 1 and 2 the connection device previously used in the machine marketed by the applicant under the name PROSTATRON®, and FIGS. 3 to 6 that shown two current preferred modes of realization of the invention provided simply as an illustration and which in no case shall limit the value of the invention. In the drawings:

FIG. 1 shows a single-piece, multifunction and hybrid connection device, utilized as part of the machine marketed by the applicant under the name of PROSTATRON®, shown by the general reference number 10, in a view that shows the front face 12 of the actual connection, while FIG. 2 shows the profile of this connection device 10 in an inverted position with respect to FIG. 1 so as to more precisely show the lower face 16.

Referring to FIGS. 1 and 2, the preceding connection device of the PROSTATRON® apparatus is a single-piece, multifunction and hybrid connection device, including a housing 11 whose form is adapted to be able to be connected to a reception device (not shown here), including a front face 12, a rear face 13, visible in FIG. 2, an upper face 14, a lower face 16 and lateral faces 17, 18 for linkage. The front face 12, that is the connection face, contains several orifices 20, 22, 23, 24, 25, 26 in which are connected various elements to connect such as 30, 32, 34, 36, including at least one electrical connection element such as 34, and at least two connection elements for a liquid, for example water or an aqueous solution, such as 30, 32, orifices 23, 24 receiving the said elements 30, 32 being arranged on the front face 12, as seen in FIGS. 1 and 2, in suitable positions to cooperate in an aligned manner with the reception connection elements of the reception connection device, as is understood by someone familiar with the technology.

In the framework of the previously marketed connection device 10 by the applicant in the PROSTATRON® apparatus, this connection device contained at least two orifices 20, 22 placed laterally, in particular with practically the same distance as the two connection elements, respectively input 32 and output 30 of a liquid, these orifices 20, 22 being used to receive two centering pins connected to the connection reception device to assure a precise alignment by the centering pins, as is understood by someone familiar with the technology.

In the previous device, orifice 25 was arranged practically in the center with respect to orifices 23, 24 receiving the sealed fluid connection elements 30, 32 that enable the transmission of a microwave radiation via a coaxial cable. In addition, orifice 26 received a connection element 36 composed of optical fibers, for example four, shown by reference number 40 in FIGS. 1 and 2, used for temperature detection, as described notably in document U.S. Pat. No. 5,480,417 of the applicant and describing the operation of the temperature detection elements, as well as the urethral probe 50 inserted in the urethra 42 of the prostate gland P, kept in place by a balloon catheter B inflated in the bladder V, as is well described in the preceding US document of the applicant. Temperature detection also occurs via a rectal probe 60 placed in the rectum R, that is also the subject of a special patent and that is also marketed in the framework of the PROSTATRON® apparatus.

Control of operation by a computer 86, controlling the emission of the microwaves device 88, of the cooling liquid circulation circuit 90, and managing temperature measurements of the device 92, have also been described in the past and are understood by someone familiar with the technology.

The connection device 10, also including a separate orifice 28, on the lower side 16 of the connection device 10, as seen in FIG. 2, for the passage of a conduit 29 for inflating the balloon catheter B of the urethral probe 50 that may include a means of closure 52, such as a valve. The balloon catheter P can be inflated with air or with a liquid such as water.

It is easily understood that the connection device 10 of the urethral probe 50 and of the rectal probe 60 with the connection reception device destined to connect the various elements to their respective control units, such as 88, 90, 92 themselves controlled by a central command unit, including for example a computer such as 86, was a very complicated design, took up a considerable volume, required the presence of centering pins leading to poor ergonomics and a hyperstatic situation, increasing the difficulties of perfect alignment of the connection elements having different functions with certain elements of circulation of a liquid in presence of electrical connection elements that are mutually incompatible. All these contradictory elements increased the risk of an incorrect alignment in particular of the optical fibers 40 with a diameter of about 200 μm, which require a precise alignment of 20 μm.

These problems are resolved by the present invention that will now be described with reference to FIGS. 3 to 7.

FIGS. 3 to 6 show an initial and currently preferred mode of realization of a connection device according to the present invention shown by the general reference number 100, with the same presentation as for the mode of realization of the connection device previously marketed by the applicant and being the object of FIGS. 1 and 2. As a result of this, the same identification numbers have been used for identical parts or functions. Thus, the urethral probe has the same general reference number 50, the rectal probe the same reference number general 60 and also for the command or regulation device, respectively microwaves 88, cooling liquid, such as water 90, temperature measurement 92 and for the central command unit 86 including for example a computer.

In the framework of the present invention, it is easily seen that the connection device 100 is fundamentally modified, is very flat, occupies a reduced volume, and has a much lower number of connection points, since in the mode of realization represented in FIGS. 3 to 6, there are three, without limitation to this number.

In the framework of the invention, the connection device 100 is characterized in that at least two of the connection elements, respectively 130, 132, with analogy to the distinct connection elements 30, 32 of the prior mode of realization, are coaxially arranged in the same orifice such as 124 of the front face 112 and cooperate with at least two connection reception elements also arranged coaxially, as in understandable to someone familiar with the technology, and which are not shown here for purposes of better clarity of the drawings.

Figure 5:
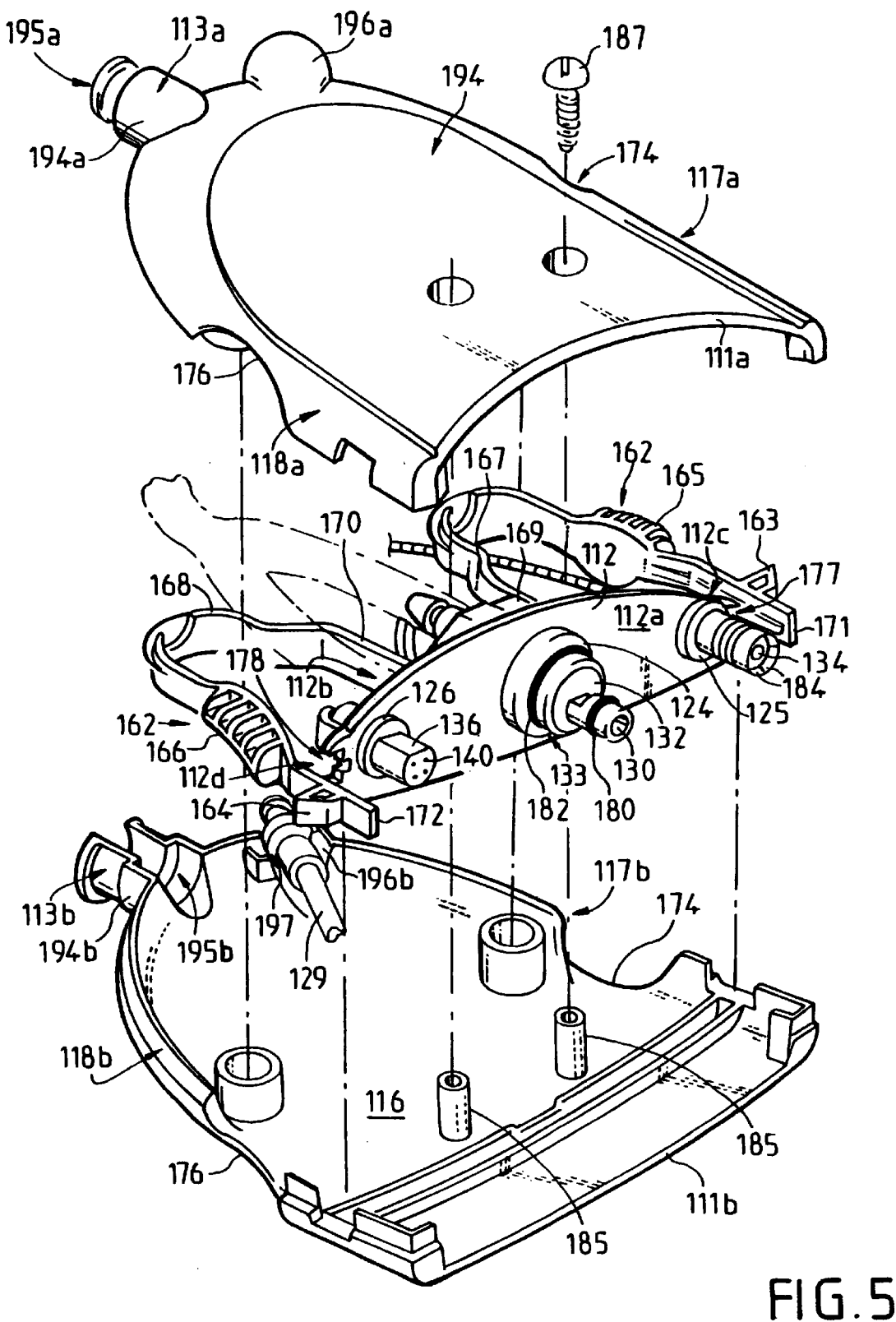
FIG. 5 is an exploded perspective view of the multifunction connection device of the present invention.
Figure 6:
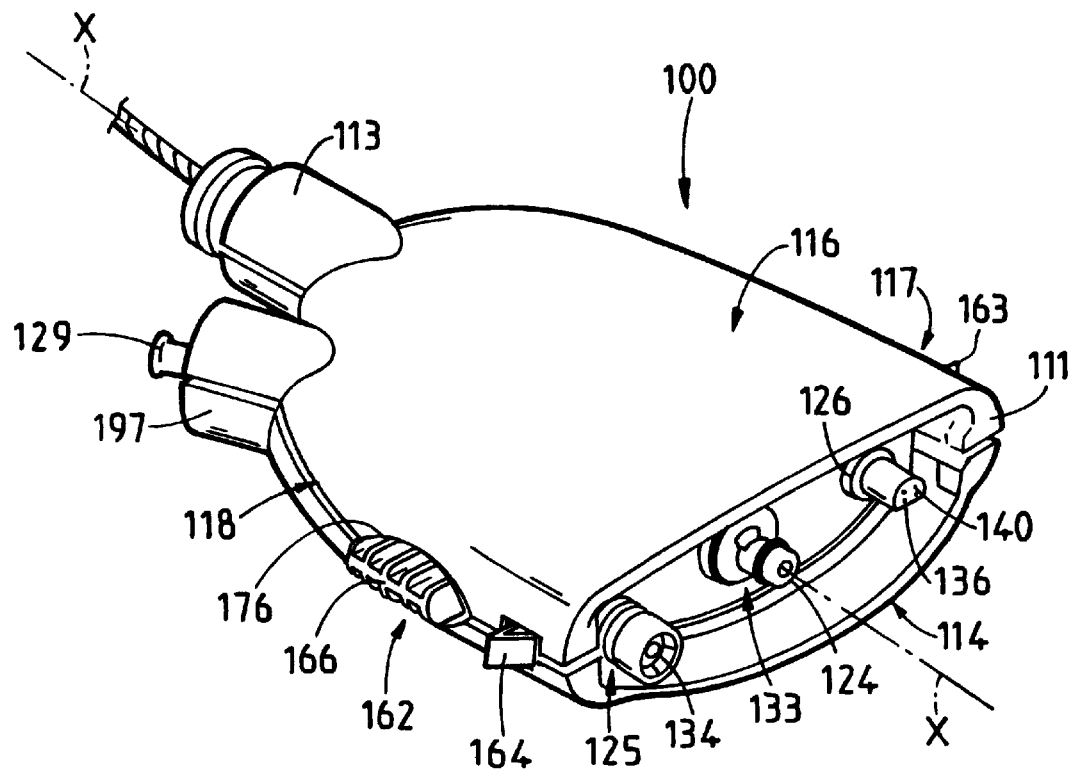
FIG. 6 is a perspective view of the multifunction connection device of the present invention.
Figure 7:
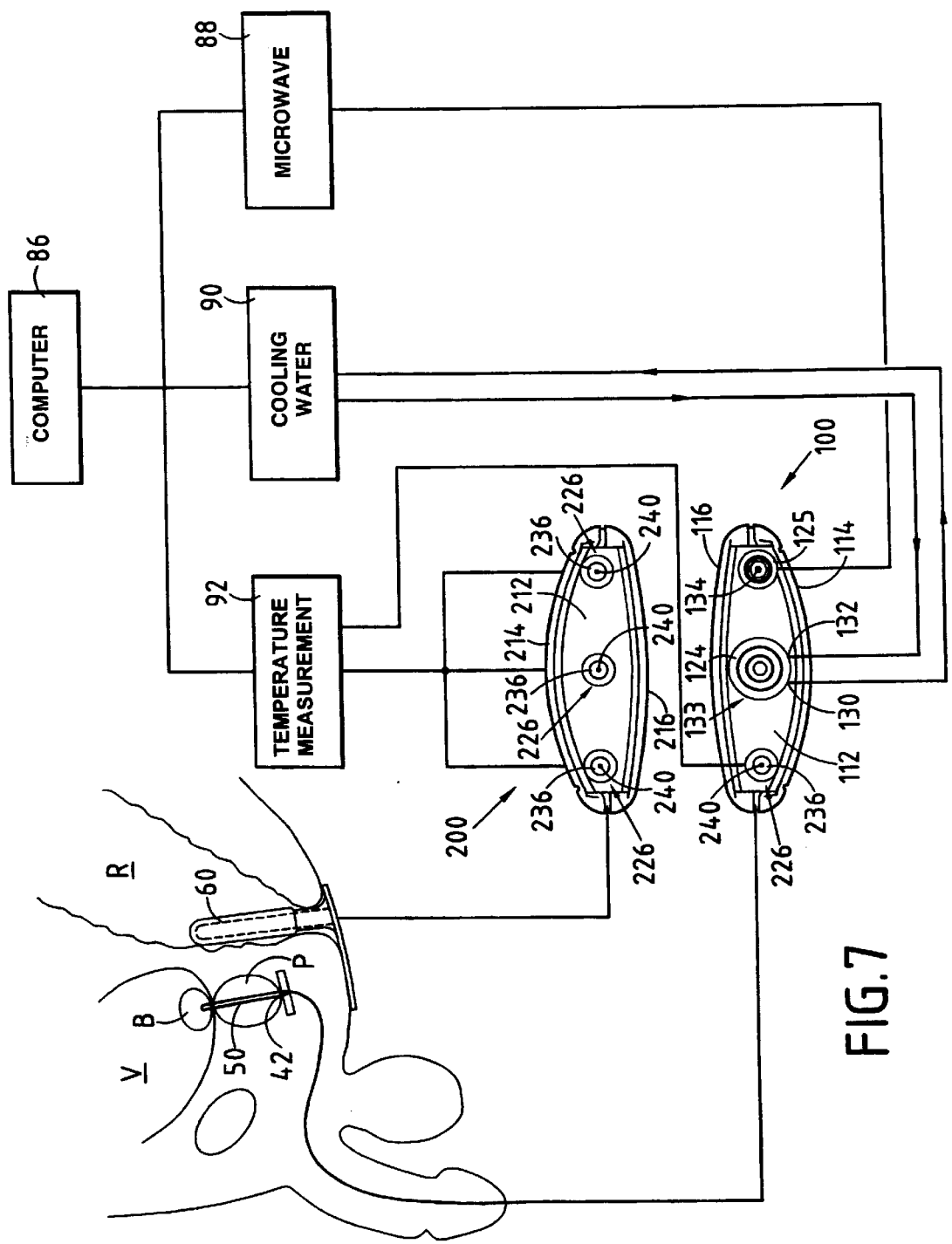
FIG. 7 is a schematic view of an alternative configuration of the multifunction connection device of the present invention.

It is to be noted that the mode of realization of FIGS. 3 to 6, as also the case for FIG. 7, is an integral part of the present invention and thus of the present description and is incorporated entirely by reference.

According to an advantageous mode of realization of the invention, the said at least two connection elements 130, 132 arranged in the same orifice 124 constitute respectively one element for the supply of a liquid and one element for draining a liquid, arranged coaxially on a single part 133 introduced in a single orifice 124 of the front face 112.

By analogy to the prior connection device in FIGS. 1 and 2, the other faces of the device present reference number 111 for the housing, 114 for the upper face, 116 for the lower face, 117 and 118 for the side faces, 113 for the rear face.

According to an advantageous mode of realization of the invention, the device 100 comprises at least four connection elements, 130, 132, 134, 136, mounted in at least three orifices 124, 125, 126 mutually separated and aligned on the front face 112 of the connection device 100, at least two connection elements, 130, 132, arranged coaxially in one, here 124, of the three aligned orifices 124, 125, 126, as is clearly visible in FIGS. 3, 5 and 6, itself constituting a patentable characteristic of the present invention.

According to yet another mode of advantageous realization of the invention, the two coaxial connection elements, here 130, 132, are mounted in a single orifice, here 124, arranged practically along the longitudinal X—X axis of the connection device 100, as shown in FIGS. 4 to 6, such that the said at least two other aligned orifices, here 125, 126, are preferentially arranged on either side of the said axial orifice 124 receiving the two coaxial connection elements 130, 132, as is well seen in the figures.

According to yet another mode of advantageous realization of the invention, the device 100 includes on at least two opposite sides of the said device, other than the front 112 and rear faces 113, for example here the side faces 117, 118, provisional means 162 of locking the connection device 100 with the corresponding reception device.

According to an advantageous mode of realization of the invention, the provisional means of locking 162 include at least a first means of locking 163 and a second means of locking 164 arranged on opposite sides of the said connection device 100, other than the front 112 and rear faces 113, here the side faces 117, 118, the said means of locking 162 being switchable between a locked position and an unlocked position, and planned to be able to control an unlocking in locked position of the connection device 100 with the reception device.

According to yet another mode of advantageous realization of the invention, the above-mentioned first and second means of locking, respectively 163, 164, include a part accessible from the outside, 165, 166 to assure unlocking without a tool.

According to yet another mode of advantageous realization of the invention, the above-mentioned provisional means of locking 162 are solidly attached to the front face 112 du device 100.

According to yet another mode of advantageous realization of the invention, the above-mentioned front face 112 and above-mentioned means of locking 162 are of single-piece construction, preferentially in plastic, the means of locking 162 being preferentially defined by an extension respectively 167, 168 inside the connection device 100, i.e. opposite the connection part of the front face 112 with the reception device, the said extension including a curve to have the extremity of the elongation be near the front face, for example here including the first means of locking 163 and the second means of locking 164, thereby presenting an elongated U shape of which one branch of the U, respectively 169, 170, is attached to the inside 112*b* of the front face 112 and the other extremity respectively 171, 172 is mobile and has at least one anchor point to constitute a locked or unlocked position depending on whether this mobile extremity is or is not anchored in the anchor point. This anchor point is defined by a corresponding reception part of the reception device, not shown here.

According to yet another mode of advantageous realization of the invention, the branch 171, 172 of the mobile U includes a reinforced zone that is an unlocking button of the connection device 100 when it is connected to the reception device, and defines the part accessible from the exterior 165, 166 described above, as is clearly seen in FIGS. 3 to 6.

According to yet another mode of advantageous realization of the invention, the free extremity 171, 172 of the branch of the mobile U includes a part radially protruding towards the exterior, defining a ratchet element constituting the above-mentioned provisional means of locking/unlocking 162 163, 164, enabling the easy introduction of the connection device in the reception device but with automatic locking once this introduction takes place and requiring an unlocking operation, for example by acting on the above-mentioned unlocking button 165, 166, accessible from the exterior and placed in a corresponding opening, here lateral 174, 176 of the connection device 100.

According to yet another mode of advantageous realization of the invention, the front face 112 includes at least on its side faces 112*c*, 112*d*, at least one notch 177, 178 that receives and guides the mobile extremity 171, 172, of the branch of the U by constituting the above-mentioned anchor point.

According to yet another mode of advantageous realization of the invention, at least one above-mentioned connection element is a connection element 136 of a temperature detection element, preferentially optical fibers 140, preferentially comprising several optical fibers 140 placed in a single connection element 136, shown as being preferentially self-centering. Advantageously, the connection element 136 for the optical fibers 140 presents at least one flat or flattened face 136*a* which provides its orientation, cooperating with a corresponding flat or flattened face of the orifice 126 of the front face 112 of the connection device 100.

According to yet another mode of advantageous realization of the invention, the above-mentioned electrical connection element, here 134, transmits electromagnetic radiation, preferentially microwaves, in particular for a therapeutic treatment of an adenoma or prostate cancer P via the rectal or urethral route, preferentially via the urethral route, as shown in FIG. 3.

According to yet another mode of advantageous realization of the invention, the electrical connection element 134 is an electrical connection element for transmitting electromagnetic radiation, preferentially microwaves, in particular for a therapeutic treatment of an adenoma or prostate cancer P via the rectal or urethral route, preferentially via the urethral route, and the liquid connection element 133 is a coaxial two-way liquid connector element for supplying liquid 132 and draining 130 liquid, without a locking device, including sealing gaskets and a means for tightening play, visible in FIG. 5 and referenced 180 and 182, a third connection element, here 136 planned to connect a temperature detection element, here 136, preferentially optical fibers 140, all of these elements cooperating to preferentially realize a therapeutic treatment, in particular a treatment of an adenoma or prostate cancer P, with control of heating temperature resulting from the electromagnetic radiation, preferentially microwaves, by the said liquid, using elements or devices 88, 90, 92 even controlled by the control center 86, this control being familiar to someone acquainted with the technology, in particular from the PROSTATRON® apparatus previously marketed by the applicant.

According to yet another mode of advantageous realization of the invention, the device includes only three connection points, here shown by the three connection elements 133, 134, 136, aligned on the front face 112 of the connection device, including one electrical connection point 134, one coaxial connection point for two water channels 133, and one temperature measurement connection point 136, preferentially via optical fibers.

These characteristics are also patentable themselves.

According to yet another mode of advantageous realization of the invention, at least some of the connection elements 133, 134 and 136 are equipped with a device for not constraining play. Again preferentially, the connection device according to the invention has only one fixed connection point defined by a connection element having a precise connection, here connection element 136, the other connection elements, here 134 and 133 being relatively imprecise connection elements, equipped with devices for not constraining play. These devices for not constraining play may, for example, include a device with sealing gaskets such as gaskets 180, 182, such as O-rings for the water connection element(s) 130, 132, or a blade device 184, or similar, well known to someone familiar with the technology, for example for the connection of transmission elements for electromagnetic radiation, preferentially microwaves.

In this preferred mode of realization including only one fixed connection point, here by connection element 136, ergonomics of the connection are considerably simplified, preventing or limiting a hyperstatic situation. This construction is a patentable characteristic of the invention in itself.

According to yet another mode of advantageous realization of the invention, device 100 is composed of two complementary elements 111*a*, 111*b*, well seen in FIG. 5, defining the housing 111, mutually lockable by means of locking such as 185, 187, for example nut and bolt, or equivalent means, well known to someone familiar with the technology. These two complementary elements 111*a*, 111*b*, define the upper 114, lower 116, side 117, 118 and rear 113 faces of the connection device 100, resulting the said device being single-piece, the said front face 112 preferentially here defined by a separate piece, well seen in la FIG. 5 that includes the above-mentioned provisional means of locking 162.

According to yet another mode of advantageous realization of the invention, the two complementary elements 111*a*, 111*b* mutually lockable and defining the above-mentioned connection device 100 have an asymmetrical structure, i.e. the plane of junction is not a plane of symmetry of the device 100, in order to ensure a prepositioning of the connection device with the reception device, thereby assuring foolproof connection to avoid reverse connection, i.e. at 180°. Advantageously, the external surface of each of these two mutually lockable complementary elements 111*a*, 111*b* is used for pre-guiding for a better presentation of the above-mentioned connection elements in relation to the reception device. In the framework of the invention, it is possible and preferred to construct the connection device 100, and possibly the reception device, in a synthetic material, in particular a plastic, without reducing the precision of the connection even in the case where one connection element at least is used for the connection of optical fibers, as here element 136, which is a particularly unexpected advantage of the invention.

According to yet another mode of advantageous realization of the invention, the two above-mentioned complementary elements 111a, 111b include at least one flared part 194a, 196a, 194b, 196b, at least one output orifice 195, 197 on the rear facet 113. An output orifice such as 195 can be advantageously used for passing therapeutic treatment probe such as probe 50 including at least one element emitting electromagnetic radiation, preferentially microwaves, at least one element for supplying liquid in liaison with the connection element 132 and at least one element for draining liquid in liaison with the connection element 130 arranged coaxially, and at least one temperature detection element in liaison with the connection element 136, preferentially by optical fibers 140.

According to yet another mode of advantageous realization of the invention, the two complementary elements 111a, 111b include at least one second flared part 196a, 196b that by mutual cooperation define a second output orifice 197 towards the rear face 113 of the device 100, for receiving a conduit 129, similar to conduit 29, FIG. 2, for inflating the balloon catheter B planned for the front extremity of the above-mentioned therapeutic treatment probe 50 including or on which can be attached a tap or valve system such as tap 52, FIG. 2, and which enables inflation, for example with a syringe 199, or equivalent means.

According to another advantageous aspect of the invention, a therapeutic treatment device includes a multi-function connection device, this device being preferentially adapted for a therapeutic treatment of an adenoma or prostate cancer, in particular by an electromagnetic radiation preferentially with microwaves, via the rectal or urethral route.

It is understood that as a result of this invention, in particular as a result of the single part constituting the front face 112, it is possible to position in a very simple, aligned and precise manner only three connection points of which preferentially one, here connection point 136, is very precise, or fixed, which considerably simplifies the connection operation by preventing any hyperstatic problem.

According to the second mode of realization shown in FIG. 7, there may be an initial connection device 100 exclusively dedicated to the urethral probe 50, with all elements being identical to those of the mode of shown in FIGS. 3 to 6, except for the fact that the optical fibers connection element 136 of the first mode of realization is replaced here by a connection element 236 that includes only one optical fiber 240, instead of four as in the first mode of realization in FIGS. 3 to 6, this optical fiber being incorporated in the urethral probe 50. In this case, the rectal probe 60, that identically includes three optical fibers for rectal temperature detection, can be connected here to three distinct optical connection elements 236, for the connection of a single optical fiber 240, placed in a second connection device 200 similar to the first connection device 100, the only exception arising from the fact that its front face 212 contains three orifices adapted to lodging connection elements 236 of a single optical fiber. It is understood that the operation of the therapeutic treatment device remains the same.

On the contrary, this second mode of realization of the invention leads to the compete separation of the feed connections of the urethral probe 50 and including the connection device 100, and the connections of the rectal probe 60 including the connection device 200. In addition, the presence of a second connection device 200 is such that the optical fibers connection elements include only one optical fiber, which simplifies the alignment of the optical fibers. Furthermore, the feed connections of the rectal probe 60 are independent of the feed connections of the urethral probe 50, and so it is possible to assure for example a mixed use of these devices, the urethral probe device 50 with its feed connections including the connection device 100 that can be single-use or disposable, whereas the rectal probe 60 and its feed connections including the connection device 200 can be reusable.

The invention thus considerably improves the design and operation of instruments for therapeutic treatment, in particular prostate treatment.

Naturally, the connection device according to the invention can be used for other applications, these connection devices being patentable in themselves.

The invention naturally covers all means constituting technical equivalents of the means described and shown. In addition, as previously indicated, FIGS. 3 to 7 are an integral part of the present invention and thus of the description.

What is claimed is:

1. A method of treating an adenoma or prostate cancer, the method comprising:

providing a multi-function connection device having a housing whose shape is suited to be connected to a reception device, wherein the housing comprises a front face including several orifices in which are inserted various elements to connect in a sealed manner, wherein the orifices include at least one electrical connection element and at least two liquid connection elements, wherein the orifices are spaced on the front face in positions suitable for aligned cooperation with corresponding reception elements on the reception device, and wherein at least two of the connection elements are arranged coaxially in the same orifice and cooperating with at least two reception connection elements also placed coaxially:

operably connecting a first probe to the multi-function connection device through the at least one electrical connection element;

operably connecting a second probe to the multi-function connection device through the at least two liquid connection elements;

emitting microwave radiation from the first probe proximate the adenoma or prostate cancer; and circulating a coolant through the second probe proximate to cool tissue located proximate the first probe.

2. Therapeutic treatment device comprising a multi-function connection device having a housing whose shape is suited to be connected to a reception device, wherein the housing comprises a front face including several orifices in which are inserted various elements to connect in a sealed manner, wherein the orifices include at least one electrical connection element and at least two liquid connection elements, wherein the orifices are spaced on the front face in positions suitable for aligned cooperation with corresponding reception elements on the reception device, and wherein at least two of the connection elements are arranged coaxially in the same orifice and cooperating with at least two reception connection elements also placed coaxially, wherein the device is adapted for the therapeutic treatment of an adenoma or prostate cancer (P), in particular by electromagnetic radiation via a rectal or urethral route.

3. A multifunction connection device having a housing whose shape is suited to be connected to a reception device, the housing comprising a front face including several orifices in which are inserted various elements to connect in a sealed manner, the orifices including at least one electrical connection element and at least two liquid connection elements, the orifices are spaced on the front face in positions suitable for aligned cooperation with corresponding reception elements on the reception device, wherein at least two of the connection elements are arranged coaxially in the same orifice and cooperating with at least two reception connection elements also placed coaxially.

4. The device according to claim 3, wherein the at lest two connection elements placed in the same orifice, constitute respectively an element for supplying a liquid and an element for draining a liquid, coaxially arranged on a single piece placed in a single orifice of the front face.

5. The device according to claim 3, wherein the device includes at least four connection elements installed in at least three orifices mutually separated and aligned on the front face of the connection device, wherein at least two connection elements being arranged coaxially in one of the three aligned orifices.

6. The device according to claim 5, wherein the two coaxial connection elements are installed in a single orifice arranged substantially along a longitudinal axis of the connection device such that the at least two other aligned orifices are arranged on either side of the axial orifice receiving the two coaxial connection elements.

7. The device according to claim 3, wherein the device includes means of locking the connection device with the reception device.

8. The device according to claim 7, wherein the means of locking includes at least an initial means of locking and a second means of locking arranged on two opposing sides of the connection device, wherein the means of locking are moveable between a locking position and an unlocked position.

9. The device according to claim 8, wherein the first and second means of locking include a part accessible from the outside to assure an unlocking without a tool.

10. The device according to claims 7, wherein the means of locking are attached to the front face of the connection device.

11. The device according to claim 10, wherein the front face and the means of locking are formed as single-piece, wherein the means of locking is defined by an extension inside the connection device, wherein the extension includes a curvature so that the extremity of the extension is situated proximate the front face, thus presenting an elongated U shape of which one branch of the U is attached to the inside of the front face and the other extremity is mobile and has at least one anchor point to constitute a locked or unlocked position depending on whether this mobile extremity is or is not anchored in the anchor point.

12. The device according to claim 11, wherein the branch of the mobile U includes a reinforced zone that is a command button for unlocking the connection device when the device is connected to the reception device.

13. The device according to claim 12, wherein the free extremity of the branch of the mobile U includes a part that protrudes radially towards the outside defining a ratchet element for the easy introduction of the connection device in the reception device but with automatic locking once this introduction is done and requiring an unlocking operation.

14. The device according to claim 13, wherein the front face includes at least one notch for receiving and guiding the mobile extremity of the branch of the U by constituting the anchor point.

15. The device according to claim 3, wherein at least one of the connection elements is a connection element of a temperature detection element.

16. The device according to claim 15, wherein the connection element presents at least one flat face that provides orientation, cooperating with a corresponding flat face of the orifice of the front face of the connection device.

17. The device according to claim 3, wherein the electrical connection element transmits electromagnetic radiation.

18. The device according to claim 3, wherein the electrical connection element is an electrical connection element for the transmission of electromagnetic radiation and the liquid connection element is a coaxial liquid connector for supplying and draining liquid, including sealing gaskets and a means for tightening, a third connection element for connecting a temperature detection element, wherein all of these elements cooperating to realize a therapeutic treatment, in particular treatment of an adenoma or prostate cancer, with control of heating temperature resulting from the electromagnetic radiation by the liquid.

19. The device according to claim 3, wherein the device includes only three connection points aligned on the front face of the connection device, including one electrical connection point, one coaxial connection point for two water channels, and one connection point for temperature measurement.

20. The device according to claim 3, wherein the device is constructed as two complementary elements mutually lockable and defining an upper face, a lower face, side faces and a rear face, and wherein the front face is defined by a separate part that includes the provisional means of locking.

21. The device according to claim 20, wherein the two complementary elements include at least one flared part defining by complementarity an output orifice on a rear face of a probe for therapeutic treatment including at least one element that emits electromagnetic radiation at least one element for the supply of a liquid and at least one element for draining a liquid arranged coaxially and at least one temperature detection element.

22. The device according to claim 21, wherein the two complementary elements include at least one second flared part that by mutual cooperation define a second output orifice towards the rear face of the device for the reception of a conduit for inflating a balloon catheter on the front extremity of the therapeutic treatment probe including or on which can be attached a tap or valve system.

23. A therapeutic treatment apparatus comprising a multifunction connection device as defined in claim 3, wherein the apparatus is adapted for the therapeutic treatment of an adenoma or prostate cancer, in particular by electromagnetic radiation via the rectal or urethral route.

* * * * *